United States Patent [19]

Penny

[11] Patent Number: 5,395,352
[45] Date of Patent: Mar. 7, 1995

[54] Y-ADAPTOR MANIFOLD WITH PINCH VALVE FOR AN INTRAVASCULAR CATHETER

[75] Inventor: William H. Penny, St. Anthony, Minn.

[73] Assignee: SciMed Lift Systems, Inc., Maple Grove, Minn.

[21] Appl. No.: 184,888

[22] Filed: Jan. 21, 1994

Related U.S. Application Data

[63] Continuation of Ser. No. 840,167, Feb. 24, 1992, abandoned.

[51] Int. Cl.⁶ .............................................. A61M 5/00
[52] U.S. Cl. ...................... 604/256; 604/167; 604/169; 604/283; 604/284; 251/4; 251/342; 137/606
[58] Field of Search ................... 604/9, 30, 34, 82, 83, 604/86, 247, 250, 256, 283–284, 905, 167, 169; 251/4, 342; 137/606

[56] References Cited

U.S. PATENT DOCUMENTS

| | | | |
|---|---|---|---|
| 274,447 | 3/1883 | Kennish . | |
| 820,987 | 5/1906 | Perotti | 604/250 |
| 2,755,060 | 7/1956 | Twyman . | |
| 3,547,119 | 12/1970 | Hall | 604/164 |
| 3,889,675 | 6/1975 | Stewart | 604/34 |
| 3,965,925 | 6/1976 | Gooch | 251/4 |
| 3,985,140 | 10/1976 | Harris | 604/250 |
| 4,000,739 | 1/1977 | Stevens | 604/167 |
| 4,096,860 | 6/1978 | McLaughlin | 128/214.4 |
| 4,240,411 | 12/1980 | Hosono | 128/4 |
| 4,267,835 | 5/1981 | Barger et al. | 604/250 |
| 4,424,056 | 1/1984 | Urquhart et al. | 604/56 |
| 4,426,062 | 1/1984 | Bowron | 251/7 |
| 4,436,516 | 3/1984 | Olschewski et al. | 604/256 |
| 4,468,224 | 8/1984 | Enzmann et al. | 604/247 |
| 4,511,352 | 4/1985 | Theeuwes et al. | 604/56 |
| 4,547,187 | 10/1985 | Kelly | 604/284 |
| 4,598,707 | 7/1986 | Agdanowski et al. . | |
| 4,690,375 | 9/1987 | Vorhis | 251/342 |
| 4,795,426 | 1/1989 | Jones | 604/51 |
| 4,816,020 | 3/1989 | Brownell | 604/283 |
| 4,909,798 | 3/1990 | Fleischhacker et al. | 604/256 |
| 4,917,668 | 4/1990 | Haindl | 604/167 |
| 4,932,938 | 6/1990 | Goldberg et al. | 604/96 |
| 4,944,732 | 7/1990 | Russo | 604/247 |
| 4,946,133 | 8/1990 | Johnson et al. | 251/149.1 |
| 4,950,257 | 8/1990 | Hibbs et al. | 604/265 |
| 4,960,412 | 10/1990 | Fink | 604/167 |
| 4,968,294 | 11/1990 | Salama | 604/247 |
| 5,059,178 | 10/1991 | Ya | 604/101 |
| 5,071,104 | 12/1991 | Witt et al. | 604/142 |
| 5,201,725 | 4/1993 | Kling | 604/82 |

FOREIGN PATENT DOCUMENTS 0244955 11/1987 European Pat. Off. .
269907 2/1914 Germany .

Primary Examiner—C. Fred Rosenbaum
Assistant Examiner—Mark Bockelman
Attorney, Agent, or Firm—Kinney & Lange

[57] ABSTRACT

A Y-adaptor manifold assembly includes a main tubular segment adapted to be coupled to an intravascular catheter. A first, tubular side port is joined to the main tubular segment so as to be in fluid communication with a through passage of the main tubular member. The first side port forms an infusion port for radiopaque dye. A second, tubular side port is joined to the main tubular segment so as to be in fluid communication with a through passage of the main tubular member. The second side port and main tubular segment are adapted to receive dilatation catheters. To prevent backbleeding, the second side port and main tubular segment include passive hemostatic valve mechanisms. Each valve mechanism includes a valve member and a disk valve. The valve member has a normally closed, sealed state, an open state and an in-use sealed state. The valve member has an inherent tendency to move to its normally closed, sealed state or its in-use state (wherein the valve member conforms about the dilatation catheter). Application of a compressive radial force moves the valve member to its open state.

20 Claims, 2 Drawing Sheets

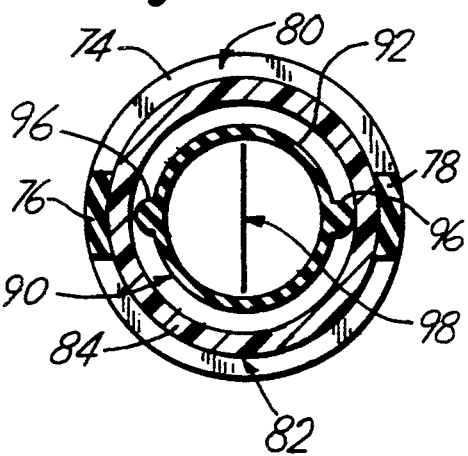
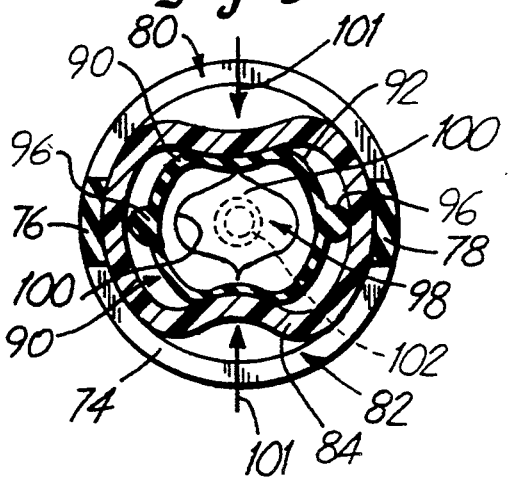
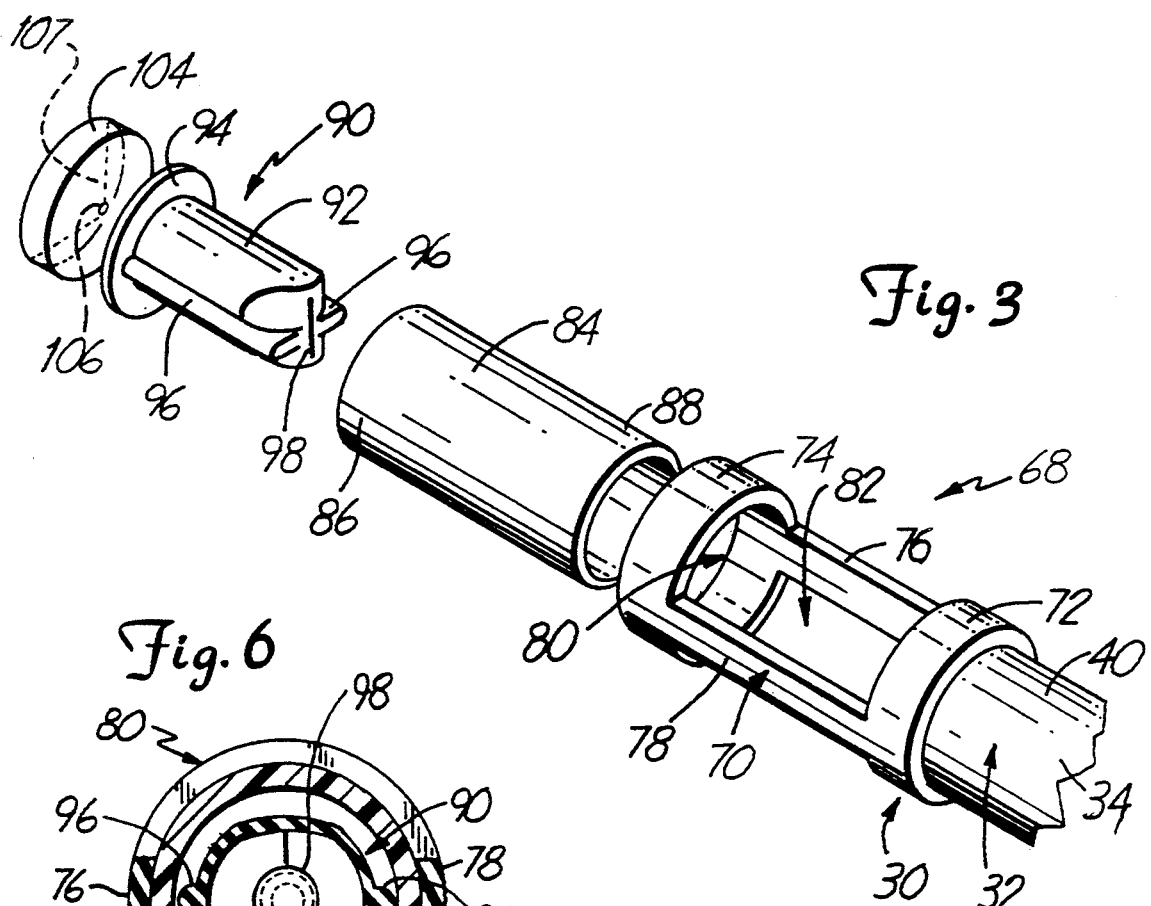
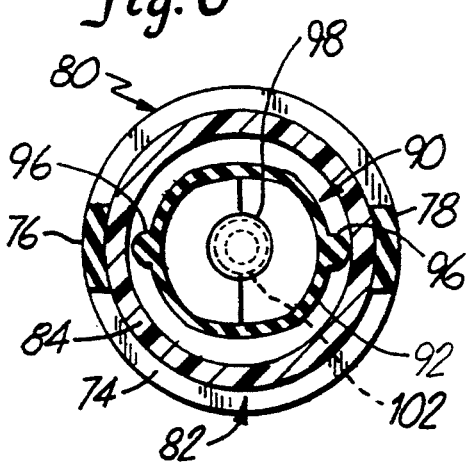

Y-ADAPTOR MANIFOLD WITH PINCH VALVE FOR AN INTRAVASCULAR CATHETER

This is a continuation of application Ser. No. 07/840,167, filed Feb. 24, 1992, now abandoned.

BACKGROUND OF THE INVENTION

The present invention relates to the field of angioplasty. In particular, the present invention is a Y-adaptor manifold assembly having passive hemostatic valve mechanisms.

Angioplasty has gained wide acceptance in recent years as an efficient and effective method for treating various types of vascular diseases. In particular, angioplasty is widely used for opening stenoses in the coronary arteries, although it is also used for treatment of stenoses in other parts of the vascular system.

The most widely used form of angioplasty makes use of a guide catheter positioned within the vascular system of a patient. The distal end of the guide catheter is inserted into the femoral artery located in the groin of the patient and pushed distally up through the vascular system until the distal end of the guide catheter is located in the ostium of the coronary artery. The distal end of the guide catheter is normally curved so that the distal tip of the guide catheter is more easily directed to the coronary ostium of the patient. Typically, a Y-adaptor manifold assembly 10 such as shown in prior art FIG. 1 is releasably secured to the proximal end of the guide catheter. The proximal end of the guide catheter and the manifold assembly 10 protrude outside the patient's body. The manifold assembly 10 provides an entryway for subsequent insertion of additional angioplasty devices into the patient's vascular system through the guide catheter. The additional angioplasty devices include dilatation catheters such as non-over-the-wire and over-the-wire balloon catheters.

The prior art Y-adaptor manifold assembly 10 shown in FIG. 1 typically includes a main body portion 12 that is secured at its distal end to the guide catheter via a luer fitting 14. The manifold assembly 10 further includes a first side branch 16 that defines an infusion port, and a second side branch 18 that is configured to receive a dilatation balloon catheter. The main body portion 12 of the manifold assembly 10 is likewise configured to receive a dilatation balloon catheter. The second side branch 18 and main body portion 12 allow two balloon catheters to be inserted into a patients' arteries so that plural stenoses can be dilated at the same time. Typically, a longitudinal axis 15 of the second side branch 18 forms an angle of thirty degrees or forty-five degrees with respect to a longitudinal axis 17 of the main body portion 12.

Proximal ends of the second side branch 18 and the main body portion 12 include valves known as Tuohy-Borst seals 20 that minimize backbleeding. Each Tuohy-Borst seal 20 includes a gasket 22 having a through aperture 24 and a threadably attached cap 26. The through aperture 24 is configured to receive a shaft of the dilatation catheter. The cap 26 can be rotatably tightened to compress the gasket 22 thereby decreasing the diameter of the through aperture 24 to form a fluid tight seal about the shaft of the dilatation catheter. However, if the cap 26 of the Tuohy-Borst seal 20 is tightened too much, the dilatation catheter may be damaged or the flow of inflation fluid through the catheter may be restricted so as to make inflation of the balloon of the dilatation catheter difficult. On the other hand, tightening the cap 26 too little may allow backbleeding through the proximal ends of the second side branch 18 and the main body portion 12 of the manifold assembly 10.

There is a continuing need for improved Y-adaptor manifold assemblies. Specifically, there is a need for a manifold assembly of efficient design which incorporates a valve member that provides an effective releasable seal about the shaft of a dilatation catheter. The valve member would provide a fluid tight seal about the dilatation catheter to prevent backbleeding, while minimizing damage to the catheter. In addition, the seal formed by the vale member would not restrict the flow of inflation fluid through the dilatation catheter.

SUMMARY OF THE INVENTION

The present invention is a manifold assembly for an intravascular catheter that is adapted to be introduced into a vascular system of a patient. The manifold assembly includes a main tubular segment having a proximal end, a distal end and a through passage. The through passage is in fluid communication with a through lumen of the intravascular guide catheter which is coupled to the distal end of the main tubular segment. A first, tubular side port is joined to the main tubular segment. The first side port has a through passage in fluid communication with the through passage of the main tubular segment. A second tubular side port is joined to the main tubular segment. The second side port also has a through passage in fluid communication with the through passage of the main tubular segment. A passive hemostatic valve mechanism is coupled to the proximal ends of each of the main tubular segment and the first tubular side port.

Each valve mechanism includes a flexible valve member, such as a duck-bill valve. The valve member has a through opening defined by a movable sealing side wall which has a normally closed, sealed state that prevents backbleeding out of the respective through passageway, and an open state wherein a medical device, such as a dilatation catheter, can be inserted into the respective through passageway through the through opening of the valve member. The sealing wall is movable from the normally closed, sealed state to the open state by applying a compressive radial force to the valve member.

The sealing wall of the valve member has a further in-use sealed state wherein the sealing wall conforms about the medical device so as to prevent backbleeding out of the respective through passageway. The sealing wall is movable from the open state to the in-use sealed state by removing the compressive radial force from the valve member. This allows the sealing wall to conform about the medical device due to the inherent tendency of the sealing wall to move towards its normally closed, sealed state.

The valve mechanism further includes a disk valve positioned proximally of and adjacent to the valve member. The disk valve has a through aperture for receiving therethrough the medical device in the open state of the sealing wall, such that the medical device passes first through the through aperture of the disk valve and then through the through opening of the valve member.

The first and second side ports are oriented at an angle relative to a longitudinal axis of the main tubular segment. The second side port forms an angle of between ten and twenty five degrees and preferably fifteen degrees with respect to the longitudinal axis of the main tubular segment. The second side port forms an angle of approximately thirty degrees with respect to the longitudinal axis of the main tubular segment.

This Y-adaptor manifold assembly is a relatively efficient design. The passive hemostatic valve mechanisms at the proximal ends of the main tubular segment and the second side port provide an effective releasable seal about the shaft of a dilatation catheter without damaging the catheter or restricting inflation fluid flow through the dilatation catheter. Moreover, the valve mechanisms prevent backbleeding out through the proximal ends of the second side port and the main tubular segment of the manifold assembly. In addition, the relatively slight angle that the second side port forms with respect to the main tubular segment, allows a dilatation catheter to be easily steered through the side port and into the guide catheter, without kinking of the dilatation catheter sometimes associated with the use of manifolds having higher angle side branch orientations. The relatively slight angle of the second side port causes minimal flexing of the dilatation catheter in the region where the catheter passes through the manifold assembly. Minimal flexing of the dilatation catheter results in more reliable and sensitive dilatation catheter torque response when steering the catheter through the vascular system of a patient.

BRIEF DESCRIPTION OF THE DRAWINGS

FIG. 3 is an reversed, exploded perspective view of the passive valve mechanism shown in FIG. 2.

FIG. 4 is a sectional view taken along line 4—4 in FIG. 2 showing the passive valve mechanism in a normally closed, sealed state.

FIG. 5 is a sectional view similar to FIG. 4 showing the passive valve mechanism in an open state.

FIG. 6 is a sectional view similar to FIG. 4 showing the passive valve mechanism in an in-use sealed state with a dilatation catheter extending therethrough.

While the above identified figures set forth a preferred embodiment, other embodiments of the present invention are also contemplated as noted in the discussion. In all cases, this disclosure presents illustrated embodiments of the present invention by way of representation and not limitation. It should be understood that numerous other modifications and embodiments can be devised by those skilled in the art which fall within the scope and spirit of the principles of this invention. It should be noted that the figures have not been drawn to scale as it has been necessary to enlarge certain portions for clarity. In addition, the use of such relational terms as left/right, upper/lower, or horizontal/vertical, etc. are used herein for reference purposes only and are not intended to be limiting features of the invention disclosed.

DETAILED DESCRIPTION OF THE PREFERRED EMBODIMENTS

Figure 1:
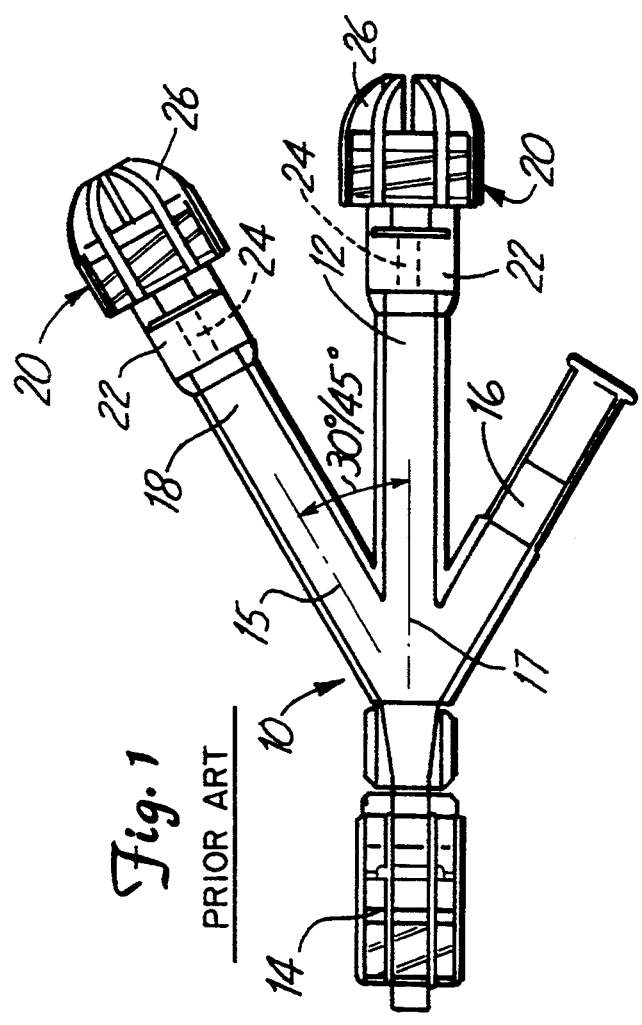
FIG. 1 is a side elevational view of a prior art Y-adaptor manifold.
Figure 2:
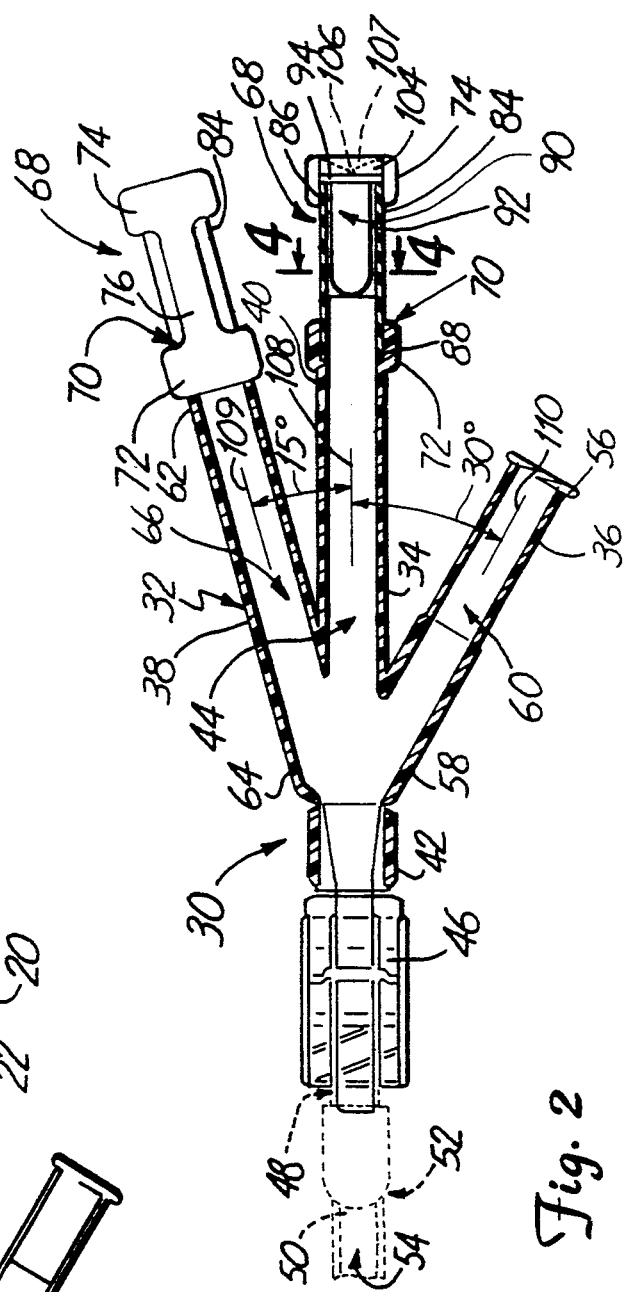
FIG. 2 is a side elevational view of a Y-adaptor manifold with a passive hemostatic valve mechanism in accordance with the present invention with some portions shown in section.

An angioplasty catheter system 30 including a Y-adaptor manifold assembly 32 in accordance with the present invention is illustrated generally in FIGS. 2 and 3. The manifold assembly 32 includes a body member (preferably formed from polycarbonate) defined by a main tubular segment 34, a first, tubular side port 36 and a second, tubular side port 38. The main tubular segment 34 has a proximal end 40, a distal end 42 and a through passage 44 extending between the proximal end 40 and the distal end 42. Joined to the distal end 42 of the main tubular segment 34 is a luer fitting 46 preferably formed from polycarbonate. The luer fitting 46 allows the manifold assembly 32 to be releasably coupled to a cooperating luer coupler 48 mounted at a proximal end 50 of an intravascular guide catheter 52. With the guide catheter 52 coupled to the manifold assembly 32, the through passage 44 of the main tubular segment 34 is in fluid flow communication with a through lumen 54 of the guide catheter 52.

The first, tubular side port 36 has a proximal end 56, a distal end 58 and a through passage 60 extending between the proximal end 56 and the distal end 58. The first side port 36 is integral with the main tubular segment 34 and is located proximally of the distal end 42 of the main tubular segment 34. The through passage 60 of the first side port 36 is in fluid flow communication with the through passage 44 of the main tubular segment 34 and thereby the through lumen 54 of the guide catheter 52. The first side port 36 is adapted to releasably receive a syringe containing a radiopaque dye that can be injected through the through lumen 54 of the guide catheter 52 (via through passage 44) to the coronary arteries within which the guide catheter 52 has been placed.

The second, tubular side port 38 has a proximal end 62, a distal end 64 and a through passage 66 extending between the proximal end 62 and the distal end 64. The second side port 38 is integrally with the main tubular segment 34 and is located proximally of the distal end 42 of the main tubular segment 34. The through passage 66 of the second side port 38 is in fluid flow communication with the through passage 44 of the main tubular segment 34 and thereby the through lumen 54 of the guide catheter 52.

The main tubular segment 34 and the second side port 38 are each adapted to receive a dilatation balloon catheter. In the main tubular segment 34, the dilatation catheter will pass straight through the through passage 44 and through the through lumen 54 of the guide catheter 52 and into the vascular system of a patient. In the second side port 38, the dilatation catheter will pass through the through passage 66, a distal portion of the through passage 44 and through the through lumen 54 of the guide catheter 52 and into the vascular system of the patient. If desired, this arrangement allows two dilatation catheters to be introduced to a patient's vascular system so that plural stenoses can be dilatated at the same time in what is known as a "Kissing Balloon" technique. To prevent backbleeding through the proximal ends 40 and 62 of the main tubular segment and second side port 34 and 38, respectively, a passive hemostatic valve mechanism 68 is mounted to each proximal end 40 and 62 of the main tubular segment and second side port 34 and 38, respectively.

As seen best in FIG. 3, each passive hemostatic valve mechanism 68 includes a support member 70 formed preferably of polycarbonate. The support member 70 includes a first annular ring 72, a second annular ring 74 spaced from the first annular ring 72 and oppositely positioned, first and second, rigid support members 76 and 78, respectively. The support members 76 and 78 define a pair of oppositely directed, upper and lower windows 80 and 82, respectively.

Each valve mechanism 68 further includes a flexible tubular sleeve 84 having a proximal end 86 and a distal end 88. The tubular sleeve 84 is formed preferably of urethane. Alternatively, the tubular sleeve 84 can be formed of silicone. The proximal end 86 of the tubular sleeve 84 is sealed and secured to an inner surface of the second annular ring 74 by an adhesive and sealing material, and the distal end 88 of the tubular sleeve 84 is sealed and secured to an inner surface of the first annular ring 72 by an adhesive and sealing material. The tubular sleeve 84 extends between the first and second annular rings 72 and 74. The adhesive and sealing material is preferably epoxy. Alternatively, cyanoacrylate can be used as the adhesive and sealing material.

As seen best in FIG. 3, each valve mechanism 68 further includes a flexible valve member, such as a duck-bill valve 90. The duck-bill valve 90 is formed preferably of urethane. Alternatively, the duck-bill valve 90 can be formed of silicone. The duck-bill valve 90 has a cylindrical main component 92 with a flange portion 94 at its proximal end. A pair of opposed ridges 96 help to maintain the shape of the main component 92. As seen in FIG. 2, the main component 92 of the duck-bill valve 90 is positioned concentrically within the tubular sleeve 84 with the flange portion 94 abutting the proximal end 84 of the tubular sleeve 84. The duck-bill valve 90 is sealed and secured to the tubular sleeve 84 and the second annular ring 74 by an adhesive and sealing material applied to the flange portion 94. The adhesive and sealing material is preferably epoxy. Alternatively, cyanoacrylate can be used as the adhesive and sealing material.

A distal end of the main component 92 of the duck-bill valve 90 has a through opening, such as longitudinal slit 98 defined by a movable sealing wall, such as opposed sealing wall portions 100 (see FIG. 5). The sealing wall portions 100 have a normally closed, sealed state (see FIG. 4) that prevents backbleeding out of the respective through passageway 44 and 66, and an open state (see FIG. 5) wherein a medical device, such as a dilatation catheter 102, can be inserted into the respective through passageway 44 and 66 through the longitudinal slit 98 of the duck-bill valve 90. The sealing wall portions 100 are movable from the normally closed, sealed state to the open state by simultaneously applying a compressive radial force defined by a pair of opposed, compressive radial force components 101 (see FIG. 5) to the duck-bill valve 90 through the tubular sleeve 84 at the pair of oppositely directed, upper and lower windows 80 and 82. The compressive radial force components 101 are applied in opposite directions substantially perpendicular to a longitudinal extent of the longitudinal slit 98. The applied compressive radial force components 101 cause the longitudinal slit 98 to open as shown in FIG. 5. The force components 101 are applied to the duck-bill valve 90 through the tubular sleeve 84 preferably via finger pressure applied by a user of the manifold assembly 32. Alternatively, the force components 101 may be applied to the duck-bill valve 90 via a rotational or sliding cam mechanism or a lever mechanism associated with each valve mechanism 68.

As seen in FIG. 6, the sealing wall portions 100 of the duck-bill valve 90 have a further in-use sealed state wherein the sealing wall portions 100 conform about the dilatation catheter 102 so as to prevent backbleeding out of the respective through passageway 44 and 66. The sealing wall portions 100 are movable from the open state (FIG. 5) to the in-use sealed state (FIG. 6) by removing the compressive radial force from the duck-bill valve 90. This allows the sealing wall portions 100 to conform about the dilatation catheter 102 (see FIG. 6) due to the inherent tendency of the sealing wall portions 100 to move towards their normally closed, sealed state.

As seen best in FIG. 3, each valve mechanism 68 further includes a disk valve 104 positioned proximally of and adjacent to the duck-bill valve 90. The disk valve 104 is preferably formed of silicone. Alternatively, the disk valve 104 can be formed of urethane. The disk valve 104 has a through aperture 106 for receiving therethrough the dilatation catheter 102 in the open state of the sealing wall portions 100, such that the dilatation catheter 102 passes first through the through aperture 106 of the disk valve 104 and then through the longitudinal slit 98 of the duck-bill valve 90. The disk valve 104 further includes a funnel portion 107 that directs the dilatation catheter 102 into the through aperture 106 of the disk valve 104. The disk valve 104 is sealed and secured to the flange portion of the duck-bill valve 90 and the second annular ring 74 by an adhesive and sealing material. The adhesive and sealing material is preferably epoxy. Alternatively, cyanoacrylate can be used as the adhesive and sealing material.

As seen in FIG. 2, the first and second side ports 36 and 38 are oriented at an angle relative to a longitudinal axis 108 of the main tubular segment 34. A longitudinal axis 109 of the second side port 38 forms an angle of between ten and twenty five degrees and preferably fifteen degrees with respect to the longitudinal axis 108 of the main tubular segment 34. A longitudinal axis 110 of the first side port 36 forms an angle of approximately thirty degrees with respect to the longitudinal axis 108 of the main tubular segment 34.

The Y-adaptor manifold assembly 32 is a relatively efficient design. The passive hemostatic valve mechanisms 68 at the proximal ends 40 and 62 of the main tubular segment 34 and the second side port 38, respectively, provide an effective releasable seal about the shaft of a dilatation catheter 102 without damaging the catheter 102 or restricting inflation fluid flow through the dilatation catheter 102. Moreover, the valve mechanisms 68 effectively prevent backbleeding out through the proximal ends 62 and 40 of the second side port 38 and the main tubular segment 34, respectively, of the manifold assembly 32. In addition, the relatively slight angle that the second side port 38 forms with respect to the main tubular segment 34, allows a dilatation catheter 102 to be easily steered through the second side port 38 and into the guide catheter 52 without the kinking of the dilatation catheter sometimes associated with the use of manifolds having higher angle side branch orientations. The relatively slight angle of the second side port 38 causes minimal flexing of the dilatation catheter 102 in the region where the catheter 102 passes through the manifold assembly 32. Minimal flexing of the dilatation catheter 102 results in more reliable and sensitive dilatation catheter torque response when steering the catheter 102 through the vascular system of a patient.

Although the present invention has been described with reference to preferred embodiments, workers skilled in the art will recognize that changes may be made in form and detail without departing from the spirit and scope of the invention.

What is claimed is:

1. A Y-adaptor manifold assembly for use with an intravascular catheter, the manifold assembly comprising:
   a body member including:
      a main tubular segment having a distal end, a proximal end and a through passage extending between the distal and proximal ends, the distal end of the main tubular segment being adapted to be joined to an intravascular catheter so that the through passage of the main tubular segment is arranged to be in fluid communication with a through lumen of the intravascular catheter;
      a valve mechanism having a frame with distal end and a proximal end with the distal end thereof fixed to the proximal end of the main tubular segment with the valve mechanism extending outwardly from the proximal end of the main tubular segment, the valve mechanism including;
         a flexible valve member fixed within the valve mechanism frame and having a longitudinal slit defined by opposed sealing wall portions, the sealing wall portions having a normally closed, sealed state that prevents a fluid medium from passing out of the through passage of the main tubular segment through the proximal end thereof, and an open state wherein a medical device can be inserted into the through passage of the main tubular segment through the longitudinal slit of the valve member, the sealing wall portions being movable from the normally closed, sealed state to the open state by way of a pair of opposed, compressive radial force components that are simultaneously applied to the valve member in opposed directions substantially perpendicular to a longitudinal extent of the longitudinal slit; and
         a flexible tubular sleeve extending between and fixed within the distal end and the proximal end of the valve mechanism frame with the sleeve extending about the valve member,
         wherein the frame of the valve mechanism is configured and arranged to support the valve member and the sleeve and to permit access to the sleeve for application of the opposed radial force components to the valve member through the sleeve; and
      a tubular side port joined to the main tubular segment proximally of the distal end of the main tubular segment, the side port having a through passage in fluid communication with the through passage of the main tubular segment.

2. The Y-adaptor manifold assembly of claim 1 wherein the sealing wall portions have an in-use sealed state wherein the sealing wall portions of the longitudinal slit conform about the medical device and a fluid medium is prevented from passing out of the through passageway of the main tubular segment through the proximal end thereof, the sealing wall portions being movable from the open state to the in-use sealed state by removing the compressive radial force components from the valve member and allowing the sealing wall portions to conform about the medical device due to the inherent tendency of the sealing wall portions to move towards their normally closed, sealed state.

3. The Y-adaptor manifold assembly of claim 1, and further including:
   a disk valve fixed within the proximal end of the valve mechanism frame proximal to the valve member, the disk valve having a through aperture wherein upon insertion of the medical device into the through passage of the main tubular segment, the medical device passes first through the through aperture of the disk valve before the medical device passes through the valve member in its open state.

4. The Y-adaptor manifold assembly of claim 3 wherein the disk valve has a funnel portion that directs the medical device into the through aperture of the disk valve.

5. The Y-adaptor manifold assembly of claim 1 wherein the valve mechanism frame further includes:
   a first annular ring defining the distal end of the valve mechanism and joined to the proximal end of the main tubular segment; and
   a second annular ring spaced from and coupled to the first annular ring, the second annular ring defining the proximal end of the valve mechanism and being configured to support the valve member, wherein a distal end of the sleeve is fixed within the first annular ring of the valve mechanism frame and a proximal end of the sleeve is fixed within the second annular ring of the valve mechanism frame.

6. The Y-adaptor manifold assembly of claim 5 wherein the valve mechanism frame further includes a pair of rigid support members joining the second annular ring to the first annular ring, the pair of support members defining a pair of oppositely directed windows to allow the opposed compressive force components to be applied to the valve member through the tubular sleeve.

7. The Y-adaptor manifold assembly of claim 6, and further including:
   a disk valve positioned within the second annular ring and proximal to the valve member, the disk valve having a through aperture wherein upon insertion of the medical device into the main tubular segment the medical device passes first through the through aperture of the disk valve before the medical device passes through the valve member in its open state.

8. A Y-adaptor manifold assembly for use with an intravascular guide catheter configured to be introduced into a vascular system of a patient, the manifold assembly comprising:
   a body member including:
      a main tubular segment having a distal end, a proximal end and a through passage extending between the distal and proximal ends, the distal end of the main tubular segment being adapted to be joined to an intravascular guide catheter so that the through passage of the main tubular segment is arranged to be in fluid communication with a through lumen of the intravascular guide catheter;
      a first side port tubular segment having a distal end and a proximal end, the distal end thereof joined to the main tubular segment, the first side port having a through passage in fluid communication with the through passage of the main tubular segment;
      a second tubular side port joined to the main tubular segment, the second side port having a through passage in fluid communication with the through passage of the main tubular segment; and a first valve mechanism having an elongate tubular frame with a distal end and a proximal end, the distal end Of the first valve mechanism frame being fixed to and extending outwardly from the proximal end of the main tubular segment and a second valve mechanism having an elongate tubular frame with a distal end and a proximal end, the distal end of the second valve mechanism frame being fixed to and extending outwardly from the proximal end of the first side port tubular segment, each of the first and the second valve mechanism frames defining a pair of windows and each of the first and second valve mechanisms including;

a flexible valve member fixed within each respective valve mechanism frame and having a longitudinal slit defined by opposed sealing wall portions, the sealing wall portions having a normally closed, sealed state that prevents backbleeding out of the respective through passage, and an open state wherein a medical device can be inserted into the respective through passage through the longitudinal slit of the valve member, the sealing wall portions being movable from the normally closed, sealed state to the open state by way of a pair of opposed, compressive radial force components that are simultaneously applied to the valve member in opposed directions substantially perpendicular to a longitudinal extent of the longitudinal slit; and a flexible tubular sleeve extending between and fixed within the distal end and the proximal ends of each respective valve mechanism frame with the sleeve extending about the respective valve member, the windows of each respective valve mechanism frame permitting access to each respective sleeve so that the compressive radial force components can be applied to the respective valve member through the respective tubular sleeve.

9. The Y-adaptor manifold assembly of claim 8 wherein the first and second side ports are oriented at an acute angle relative to a longitudinal axis of the main tubular segment.

10. The Y-adaptor manifold assembly of claim 9 wherein the first side port is oriented at an angle between ten and twenty five degrees with respect to the longitudinal axis of the main tubular segment.

11. The Y-adaptor manifold assembly of claim 10 wherein the first side port is oriented at an angle of fifteen degrees with respect to the longitudinal axis of the main tubular segment.

12. The Y-adaptor manifold assembly of claim 9 wherein the second side port is oriented at an angle of thirty degrees with respect to the longitudinal axis of the main tubular segment.

13. The Y-adaptor manifold assembly of claim 8 wherein the sealing wall portions have an in-use sealed state wherein the sealing wall portions of the longitudinal slit conform about the medical device inserted through the slit so as to prevent backbleeding out of the through passage, the sealing wall portions being movable from the open state to the in-use sealed state by removing the compressive radial force components from the valve member and allowing the sealing wall portions to conform about the inserted medical device due to the inherent tendency of the sealing wall portions to move towards their normally closed, sealed state.

14. The Y-adaptor manifold assembly of claim 8 wherein each of the first and the second valve mechanism frames further includes:

a first annular ring defining the distal end of each valve mechanism frame and joined to the proximal end of the respective tubular segment; and a second annular ring spaced from and coupled to the first annular ring, the second annular ring defining the proximal end of each valve mechanism frame and being configured to support the respective valve member, wherein a distal end of each respective sleeve is fixed within the first annular ring of each respective valve mechanism frame and a proximal end of each respective sleeve is fixed within the second annular ring of each respective valve mechanism frame.

15. The Y-adaptor manifold assembly of claim 14 wherein each valve mechanism frame further includes a pair of rigid support members joining the second annular ring to the first annular ring, the pair of support members defining the pair of windows to allow the opposed compressive force components to be applied to the valve member through the tubular sleeve.

16. The Y-adaptor manifold assembly of claim 15 wherein each valve mechanism frame further includes:

a disk valve positioned within the second annular ring and proximally adjacent to the valve member, the disk valve having a through aperture wherein upon insertion of a medical device into the respective through passage the medical device passes first through the through aperture of the disk valve before the medical device passes through the valve member in its open state.

17. A Y-adaptor manifold assembly for use with an intravascular catheter, the manifold assembly comprising:

a body member including:
a main tubular segment having a distal end, a proximal end and a through passage extending between the distal and proximal ends, the distal end of the main tubular segment being adapted to be joined to an intravascular catheter so that the through passage of the main tubular segment is arranged to be in fluid communication with a through lumen of the intravascular catheter;

a valve mechanism having an elongate tubular frame with a distal end and a proximal end, the distal end of the valve mechanism frame being fixed to the proximal end of the main tubular segment and the frame having a pair of windows formed therein, the valve mechanism including;

a flexible valve member disposed within the frame of the valve mechanism and having a longitudinal slit defined by opposed sealing wall portions, the sealing wall portions having a normally closed, sealed state that prevents a fluid medium from passing out of the through passage of the main tubular segment through the distal end thereof, an open state wherein a medical device can be inserted into the through passage of the main tubular segment through the longitudinal slit of the valve member and an in-use sealed state wherein the sealing wall portions of the longitudinal slit conform about the medical device to prevent the fluid medium from passing out of the through passage of the main tubular segment through its proximal end, the sealing wall portions being movable from the normally closed, sealed state to the open state by way of a pair of opposed, compressive radial force components that are simultaneously applied to the valve member in opposed directions substantially perpendicular to a longitudinal extent of the longitudinal slit, and the sealing wall portions being movable from the open state to the in-use sealed state by removing the compressive radial force components from the valve member to allow the sealing wall portions to conform about the medical device due to the inherent tendency of the sealing wall portions to move toward their normally closed, sealed state; and a flexible tubular sleeve extending between and fixed within the distal end and the proximal end of the valve mechanism frame and extending about a portion of the valve member, wherein the windows in the frame permit access of the user's fingers to the sleeve for manual application of the opposed radial force components to the valve member through the sleeve; and a tubular side port joined to the main tubular segment proximally of the distal end of the main tubular segment, the side port having a through passage in fluid communication with the through passage of the main tubular segment.

18. A Y-adaptor manifold assembly for use with an intravascular catheter, the manifold assembly comprising:

a body member include:

a main tubular segment having a distal end, a proximal end and a through passage extending between the distal and proximal ends, the distal end of the main tubular segment being adapted to be joined to an intravascular catheter so that the through passage of the main tubular segment is arranged to be in fluid communication with a through lumen of the intravascular catheter;

a valve mechanism having an elongate tubular frame with a distal end and a proximal end with the distal end of the valve mechanism frame fixed to the proximal end of the main tubular segment, the frame having a pair of windows formed therein, the valve mechanism including;

a flexible valve member disposed within the valve mechanism and having a longitudinal slit defined by opposed sealing wall portions, the sealing wall portions having a normally closed, sealed state that prevents a fluid medium from passing out of the through passage of the main tubular segment through the proximal end thereof, and an open state wherein a medical device can be inserted into the through passage of the main tubular segment through the longitudinal slit of the valve member, the sealing wall portions being movable from the normally closed, sealed state to the open state by way of a pair of opposed, compressive radial force components that are simultaneously applied to the valve member in opposed directions substantially perpendicular to a longitudinal extent of the longitudinal slit; and a flexible tubular sleeve extending between and fixed within the distal end and the proximal end of the valve mechanism frame with the sleeve extending about the valve member, wherein the windows of the frame permit the compressive radial force components to be applied to the valve member through the tubular sleeve;

a disk valve fixed within the valve mechanism proximal to the valve member, the disk valve having a through aperture being adapted to permit insertion of a medical device therethrough;

a tubular side port joined to the main tubular segment proximally of the distal end of the main tubular segment, the side port having a through passage in fluid communication with the through passage of the main tubular segment.

19. A Y-adaptor manifold assembly for use with an intravascular catheter, the manifold assembly comprising:

a body member including:

a main tubular segment having a distal end, a proximal end and a through passage extending between the distal and proximal ends, the distal end of the main tubular segment being adapted to be joined to an intravascular catheter so that the through passage of the main tubular segment is arranged to be in fluid communication with a through lumen of the intravascular catheter;

a valve mechanism including;

a frame having a first annular ring defining a distal end of the valve mechanism and a second annular ring defining a proximal end of the valve mechanism, the second annular ring being coupled to the first annular ring and the distal end of the valve mechanism being fixed to the proximal end of the main tubular segment with the valve mechanism frame extending outwardly from the proximal end of the main tubular segment;

a flexible valve member fixed within the valve mechanism frame and being supported by the second annular ring, the valve member having a longitudinal slit defined by opposed sealing wall portions, the sealing wall portions having a normally closed, sealed state that prevents a fluid medium from passing out of the through passage of the main tubular segment through the proximal end thereof, and an open state wherein a medical device can be inserted into the through passage of the main tubular segment through the longitudinal slit of the valve member, the sealing wall portions being movable from the normally closed, sealed state to the open state by way of a pair of opposed, compressive radial force components that are simultaneously applied to the valve member in opposed directions substantially perpendicular to a longitudinal extent of the longitudinal slit; and a flexible tubular sleeve having a distal end fixed within the first annular ring of the valve mechanism and a proximal end fixed within the second annular ring of the valve mechanism with the sleeve extending between the first and second annular ring of the valve mechanism, and the sleeve extending about the valve member so that the compressive radial force components can be manually applied to the valve member through the tubular sleeve; and a tubular side port joined to the main tubular segment proximally of the distal end of the main tubular segment, the side port having a through passage in fluid communication with the through passage of the main tubular segment.

20. The Y-adaptor manifold assembly of claim 19 wherein the valve mechanism further includes:

a pair of rigid support members joining the second annular ring to the first annular ring, the pair of support members defining a pair of oppositely directed windows to allow the opposed radial force components to be applied to the valve member through the tubular sleeve.

* * * * *

UNITED STATES PATENT AND TRADEMARK OFFICE
CERTIFICATE OF CORRECTION

PATENT NO. : 5,395,352
DATED : March 7, 1995
INVENTOR(S) : WILLIAM H. PENNY

It is certified that error appears in the above-indentified patent and that said Letters Patent is hereby corrected as shown below:

On the Title Page :

delete [73] Assignee: SciMed Lift Systems, Inc.,
Maple Grove, Minn.

insert [73] Assignee: SciMed Life Systems, Inc.,
Maple Grove, Minn.

Col. 9, line 5, delete "Of", insert --of--

Signed and Sealed this

Twentieth Day of June, 1995

Attest:

BRUCE LEHMAN

*Attesting Officer*  *Commissioner of Patents and Trademarks*